(12) United States Patent
Coen et al.

(10) Patent No.: US 7,388,070 B1
(45) Date of Patent: Jun. 17, 2008

(54) STRUCTURE-BASED APPROACH TO DESIGN OF INHIBITORS OF PROTEIN-PROCESSIVITY FACTOR INTERACTIONS

(75) Inventors: Donald Coen, Medfield, MA (US); James Hogle, Newton, MA (US); Carl Elkin, Cambridge, MA (US); Harmon J. Zuccola, Brookline, MA (US); Kristie Grove Bridges, Maynard, MA (US); Scott Lokey, Santa Cruz, CA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/959,948

(22) PCT Filed: May 12, 2000

(86) PCT No.: PCT/US00/12888

§ 371 (c)(1), (2), (4) Date: Jul. 9, 2002

(87) PCT Pub. No.: WO00/68185

PCT Pub. Date: Nov. 16, 2000

Related U.S. Application Data

(60) Provisional application No. 60/134,076, filed on May 12, 1999.

(51) Int. Cl.
- C07C 237/24 (2006.01)
- C07D 237/24 (2006.01)
- A61K 31/16 (2006.01)
- A61P 31/00 (2006.01)
- A61P 35/00 (2006.01)

(52) U.S. Cl. .................... 530/232; 560/116; 560/117

(58) Field of Classification Search ................ 530/323; 560/116, 117; 702/27
See application file for complete search history.

(56) References Cited

OTHER PUBLICATIONS

Lukas et al. J. Med. Chem., 42 (5), 910-919, Feb. 1999.*

* cited by examiner

*Primary Examiner*—Michael Borin
(74) *Attorney, Agent, or Firm*—Foley & Lardner LLP

(57) ABSTRACT

A method for the structure-based identification and selection of inhibitors of processivity factor binding to protein is disclosed herein. Characterization of the protein/processivity factor interface is given. Methods for the structure-based inhibition of processivity factor binding to protein are also given. One embodiment includes a class of peptidomimetics that mimic helical portions of proteins. In addition, methods of treatment of various diseases are given, using the inhibitors of the invention.

3 Claims, 7 Drawing Sheets

```
                        1                   19                                    36
              Ac-D D V A A R L R A A G F G A V G A G A T A E E T R R M L H R A F D T L A    Peptide A
                        1200               1218                                   1235     Pol Residues Ac-████████████████████████████████████████-NH₂                              Peptide E
```

Figure 1. Amino acid sequence of peptides A and E.

Fig 3
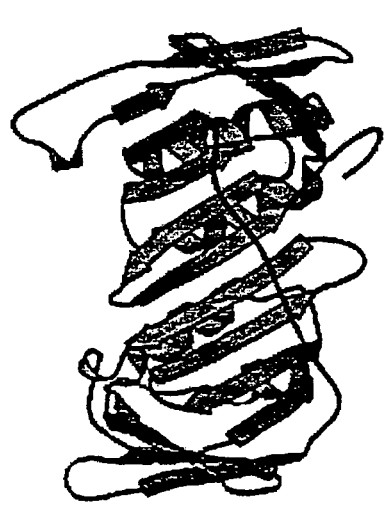 

Fig 4
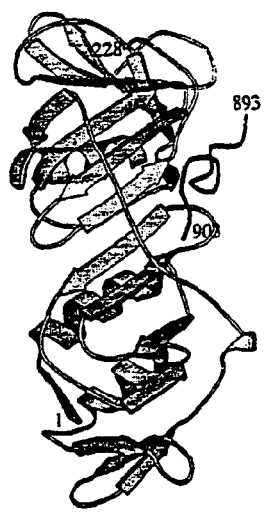
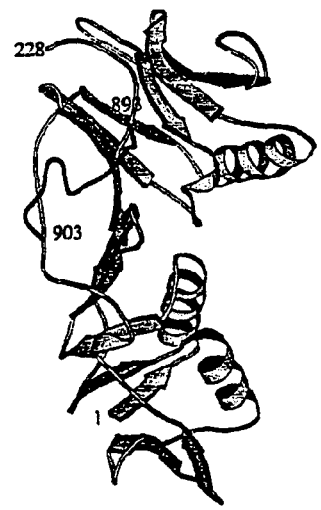
gp45
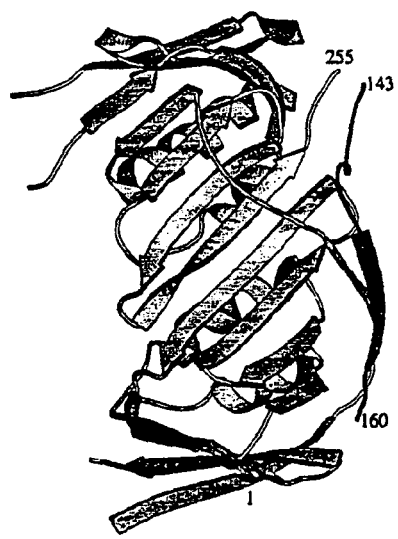
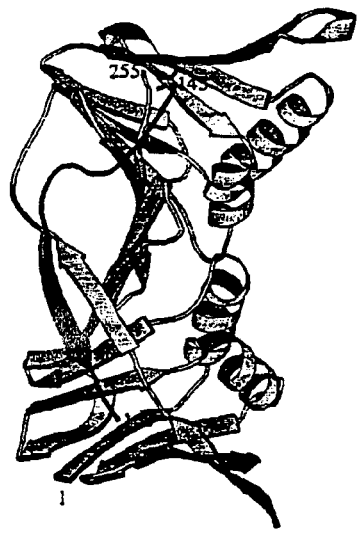
PCNA
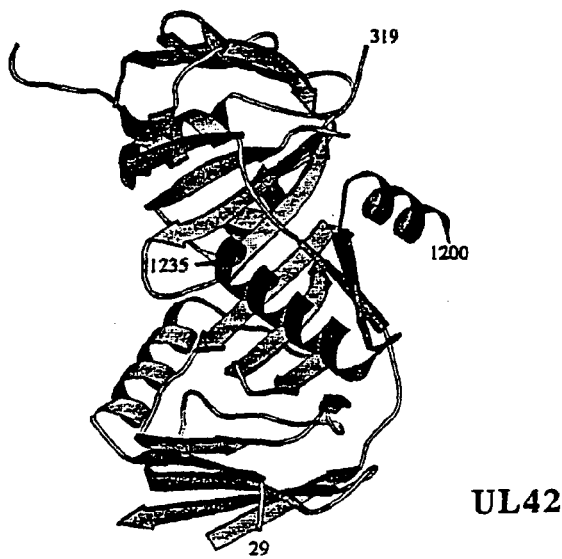
UL42

```
H  A  C  N  Q  F  N  P  S  Y  H  P
H  A  C  L  Q  F  N  P  S  Y  H  P
H  A  C  L  Q  F  N  R  S  V  H  P
T  A  P  R  L  H  Q  L  D  P  T  L  W
I  A  H  R  F  H  Q  L  D  P  T  W
         A  F  Q  T  S  P  P  S  V  R  P

UL42 (171-76)     Q  G  T  P  D  V
```

Fig. 7. Alignment of peptide display sequences with UL42. The top two lines give sequences of peptides identified by flagellar display while the remaining peptides were identified by phage display. Underlined residues are shared with a segment of UL42 shown in the bottom line.

SEQUENCE LISTING

```
<160> NUMBER OF SEQ ID NOS: 10

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:
      Illustrative spider peptide sequence

<400> SEQUENCE: 1

Glu His Asn Gln
  1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence:
      Illustrative spider peptide sequence

<400> SEQUENCE: 2

Trp Asp His Gln
  1

<210> SEQ ID NO 3
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Asp Val Ala Ala Arg Leu Arg Ala Ala Gly Phe Gly Ala Val Gly
  1               5                  10                  15

Ala Gly Ala Thr Ala Glu Glu Thr Arg Arg Met Leu His Arg Ala Phe
             20                  25                  30

Asp Thr Leu Ala
         35

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide UL42

<400> SEQUENCE: 4

Gln Gly Thr Pro Asp Val
  1               5

<210> SEQ ID NO 5
<211> LENGTH: 12
<212> TYPE: PRT
<213> ORGANISM: Artificial Sequence
<220> FEATURE:
```

```
<223> OTHER INFORMATION: Description of Artificial Sequence: Synthetic
      peptide E

<400> SEQUENCE: 5

His Ala Cys Asn Gln Phe Asn Pro Ser Val His Pro
  1               5                  10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide T20A

<400> SEQUENCE: 6

His Ala Cys Ser Gln Phe Asn Pro Ser Val His Pro
  1               5                  10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide E22A

<400> SEQUENCE: 7

His Ala Cys Ile Gln Phe Asn Arg Ser Val His Pro
  1               5                  10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide R30A

<400> SEQUENCE: 8

Thr Ala Pro Arg Leu His Gln Leu Asp Pro Thr Leu
  1               5                  10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide H29A

<400> SEQUENCE: 9

Ile Ala His Arg Phe His Gln Leu Asp Pro Thr Trp
  1               5                  10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide F32A

<400> SEQUENCE: 10

Ala Phe Gln Thr Ser Pro Pro Ser Val Arg Pro
  1               5                  10
```

STRUCTURE-BASED APPROACH TO DESIGN OF INHIBITORS OF PROTEIN-PROCESSIVITY FACTOR INTERACTIONS

CROSS-REFERENCE TO RELATED APPLICATIONS

This application is the National Phase of PCT/US00/12888, filed May 12, 2000, and published as WO 00/68185, which in turn claims priority to Provisional Patent Application No. 60/134,076, filed May 12, 1999. The entire contents of each of the aforementioned application are incorporated herein by reference.

GOVERNMENT LICENSE RIGHTS

This invention was made with government support under Grant Nos. AI07245, AI10111, AI19838, AI26077, AI32480, AI33357 awarded by the National Institutes of Health. The government has certain rights in the invention.

BACKGROUND OF THE INVENTION

1. Field of the Invention

The instant invention is drawn to a method for the structure-based design of inhibitors of DNA polymerase, and DNA repair enzymes, to methods for inhibiting DNA replication and repair, and to methods for treating viral infections, bacterial infections, fungal infections, protozoan infections, and neoplastic diseases.

2. Description of the Related Art

The herpesviruses, herpes simplex virus (HSV), and human cytomegalovirus (CMV), are two important human pathogens. HSV causes a spectrum of diseases in immunocompetent adults including debilitating genital infections, sight-threatening ocular infections and occasionally encephalitis that is also debilitating and can be fatal if untreated (Corey, L., and P. C. Spear. 1986 *N. Engl. J. Med.* 314, 686-691.). In newborns and immunosuppressed individuals such as AIDS patients, HSV infections are even more severe. CMV causes little disease in immunocompetent adults, but it is a major cause of birth defects and a major pathogen in immunosuppressed individuals, especially AIDS and transplant patients (Britt, W. J., and C. A. Alford. 1996. Cytomegalovirus, 3rd Edition ed. In Fields Virology. B. N. Fields, D. M. Knipe, P. M. Hawley, R. M. Chanock, J. L. Melnick, T. P. Monath, B. Roizman and S. E. Straus, editors. Lippincott-Raven, Philadelphia. 2493-2523). There is also evidence for a role of CMV in cardiovascular diseases (e.g., Zhou et al. 1996 *N. Engl. J. Med.* 335, 624-630.).

Ideally, a target for an antiviral drug should be a viral gene product that differs significantly from host functions and is either essential for viral replication or can activate a drug that inhibits viral replication. Most antiherpesvirus drugs developed to date have targeted herpesvirus thymidine kinases (TK) to activate drugs, and herpesvirus DNA polymerases to be inhibited by the drugs (Coen, D. M. 1992. *Sem. Virol.* 3, 3-12). For example, HSV TK, which is not essential for replication in cell culture, activates acyclovir (ACV) by phosphorylation to its monophosphate much more efficiently than do cellular enzymes. Cellular enzymes convert the monophosphate to the triphosphate, which is a selective and potent inhibitor of HSV DNA polymerase (Pol), which is essential for replication. That TK and Pol serve as selective drug targets has been established both by biochemical studies and by the isolation and analyses of drug resistant mutants (Coen, D. M. 1986 *J. Antimicrob. Chemother.* 18, 1-10).

However, nearly all drug-resistance Pol mutations map in regions encoding regions of Pol that are conserved with human cellular DNA polymerases (Coen, D. M. 1996. In Antiviral Drug Resistance. D. Richman, editor. John Wiley & Sons, Chichester. 81-102). Thus, these antiviral drugs appear to exploit only rather subtle differences between viral and cellular and polymerases. Moreover, there are HSV infections for which these drugs are not particularly efficacious and there remain concerns about the potential for toxic effects over the lifetime of a patient and the increasing number of cases in which resistance to these drugs develops (Safrin, S. 1996. In Antiviral Drug Resistance. D. D. Richman, editor. John Wiley & Sons, Chichester. 103-122).

In an alternative investigative approach, other polymerase sites are targeted for inhibition. Within this approach, it has been observed that herpesviruses require a specific interaction between HSV DNA polymerase and a processivity factor to effect synthesis of long strands of DNA. In the case of HSV, the accessory proteins, UL42, functions by increasing processivity (Gottlieb et al., 1990 *J. Virol.* 64, 5976-5987). Both Pol and UL42 are essential for virus replication and this essentiality extends to the analogous proteins encoded by other herpesviruses that have been examined. Mutations that specifically disrupt HSV Pol-UL42 interactions block long chain DNA synthesis and viral replication indicating that these interactions are essential for virus replication (Digard et al., 1993 *J. Virol.* 67, 398-406; Digard et al., 1993 *J. Virol.* 67, 1159-1168). The segment of Pol that interacts with UL42 has been mapped to the C-terminus of the enzyme by a combination of genetic and biochemical methods (Digard et al., 1993 *J. Virol.* 67, 398-406; Digard P., and Coen, D. M. 1990 *J. Biol. Chem.* 265, 17393-17396; Marsden et al., 1994 *J. Gen. Virol.* 75(Pt 11), 3127-3135.; Stow et al., 1993 *Nucleic Acids Res.* 21(1), 87-92.; Tenney et al., 1993 *J. Virol.* 67(1), 543-547.) Peptides corresponding to the C-terminal segment of Pol specifically block long chain DNA synthesis by Pol-UL42 in vitro (Digard et al., 1995 *Proc. Natl. Acad. Sci.* 92, 1456-1460; Marsden et al., 1994 *J. Gen. Virol.* 75(Pt 11), 3127-3135.) and interfere with HSV infectivity in tissue culture (Loregian et al., 1999, *Proc. Natl. Acad. Sci.* 96: 5221-5226). This segment of Pol is partially helical (Digard et al., 1995 *Proc. Natl. Acad. Sci.* 92, 1456-1460.) but there has been no information about the structure of UL42.

The best understood processivity factors are known as sliding clamps, which include the *Escherichia coli* β-subunit of DNA polymerase III, bacteriophage T4 and RB69 gp45, and the eukaryotic clamp, PCNA. These proteins do not bind directly to DNA but, rather, form multimeric rings around DNA, which permits them to slide along the template. Moreover, under physiological conditions, the association of a sliding clamp with DNA and its cognate polymerase requires auxiliary proteins that serve as "clamp loaders' (Kuriyan, J., and O'Donnell, M. 1993 *J. Mol. Biol.* 234, 915-925.). UL42 differs from sliding clamps in that it binds directly and stably to DNA and does not require additional factors to load onto Pol or DNA (Gottlieb, J., and Challberg, M. D. 1994 *J. Virol* 68, 49374945; Marsden et al., 1987 *J. Virol.* 61, 2428-2437; Powell, K. L., and Purifoy, D. J. M. 1976 *Iniervirol.* 7, 225-239; Weisshart et al., 1999 *J. Virol.* 73, 55-66). There have been two reports of structures of processivity factors bound to peptides: 1) human PCNA complexed with a 22 residue peptide derived from the C-terminus of the cell cycle checkpoint protein p21 (Gulbis et al., 1996 *Cell* 87, 297-306); and 2) gp45 from the phage RB69 complexed with a C-terminal peptide fragment of the RB69 DNA polymerase (protein data base 1B77 1B8H; Shamoo et al., 1999, Cell, 99:155-166).

Accordingly, the interaction between processivity subunits and proteins whose functions depend upon processivity factor binding, may be an especially amenable drug target relative to other protein-protein interactions. However, many protein-protein interactions involve large surfaces which involve multiple binding site interactions. Accordingly, an effective method by which structure-based design of molecules inhibiting binding between proteins and a processivity factor subunit is desired. Moreover, a method for treating infections (i.e., viral, bacterial, fungal) and methods for treating cancer and tumor growth with structure-based design inhibitors of processivity factor binding are particularly desired.

SUMMARY OF THE INVENTION

It is therefore an object of the present invention to provide methods for the structure-based design of inhibitors of processivity factor binding to proteins.

In accomplishing the foregoing object of the invention, there is provided, in accordance with one aspect of the invention, a method for inhibiting processivity factor binding to a protein whose function is modified by the binding of said processivity factor, comprising:
  (a) identifying binding sites on said protein or a processivity factor that binds to said protein;
  (b) targeting as a site for inhibition, at least one binding site, based upon the identification made in (a);
  (c) identifying a library of compounds that are capable of binding to said binding sites; and
  (d) screening said library to identify inhibitors of said binding sites.

In another aspect of the invention, there is provided, identifying and selecting potential inhibitors of processivity factor binding to a protein comprising the foregoing method of the instant invention.

In yet another aspect of the invention, there is provided, a structure-based method for method for treating a viral, bacterial or fungal mediated infection comprising administering to an animal in need thereof a compound obtained by the foregoing method of the instant invention.

In yet another aspect of the invention, there is provided, a method for treating cancer or inhibiting tumor growth comprising administering to an animnial in need thereof a compound obtained by the foregoing method of the instant invention.

In yet another aspect of the invention, there is provided, a structure-based method for identifying and selecting potential inhibitors of a DNA polymerase, comprising:
  (a) modeling a target processivity factor based on a template selected from experimentally derived processivity factor structures, wherein said modeling comprises:(i) aligning the primary sequence of said target processivity factor sequence on the sequence of said template by pair-wise, structure-based or multiple sequence alignment to achieve a maximal homology score, followed by repositioning gaps to conserve regular secondary structures; (ii) transposing said aligned sequence to the three dimensional structure of said template to derive the three-dimensional structure of said target processivity factor; (iii) subjecting the structure obtained in step (iv) to energy minimization; and (v) identifying binding sites in said model based upon corresponding binding sites from said experimentally derived processivity factor structures;
  (b) targeting as a site for inhibition, at least one amino acid in said binding site, based upon the identification made in (a);
  (c) identifying a library of compounds that are capable of binding to said binding sites; and
  (d) screening said library to identify inhibitors of said binding sites.

In yet another aspect of the invention, there is provided, a structure-based method for identifying and selecting potential inhibitors of a DNA polymerase, comprising:
  (a) modeling a target processivity factor based on a template selected from experimentally derived processivity factor structures, wherein said modeling comprises: using computer-based tools predicting secondary structure in said target based upon secondary structure in said template to provide a three dimensional model of said target; and identifying binding sites in said model based upon corresponding binding sites from said template;
  (b) targeting as a site for inhibition, at least one amino acid in said binding site, based upon the identification made in (a);
  (c) identifying a library of compounds that are capable of binding to said binding sites; and
  (d) screening said library to identify inhibitors of said binding sites.

In a preferred embodiment, the protein is a DNA polymerase.

In yet another preferred embodiment inhibitors are selected from the group consisting of a peptide, a peptidomimetic and a non-peptide small molecule.

In yet another preferred embodiment, the peptide inhibitor comprises D-amino acids.

BRIEF DESCRIPTION OF THE DRAWINGS

FIG. 1. Amino acid sequence of peptides A and E (SEQ ID NO: 3).

FIG. 3. A comparison of structure of processivity factors PCNA, gp45 and UL42.

FIG. 4. Stereoviews of processivity factors PCNA, gp45 and UL42.

FIG. 7. Alignment of peptide display sequences with UL42 (SEQ ID NO: 4). •-peptide, E (SEQ ID NO: 5), O-T20A (SEQ ID NO: 6), ■-E22A (SEQ ID NO: 7), □-R30A (SEQ ID NO: 8), ΔH29A (SEQ ID NO: 9), ▲-F32A (SEQ ID NO: 10).

DETAILED DESCRIPTION

Figure 2:
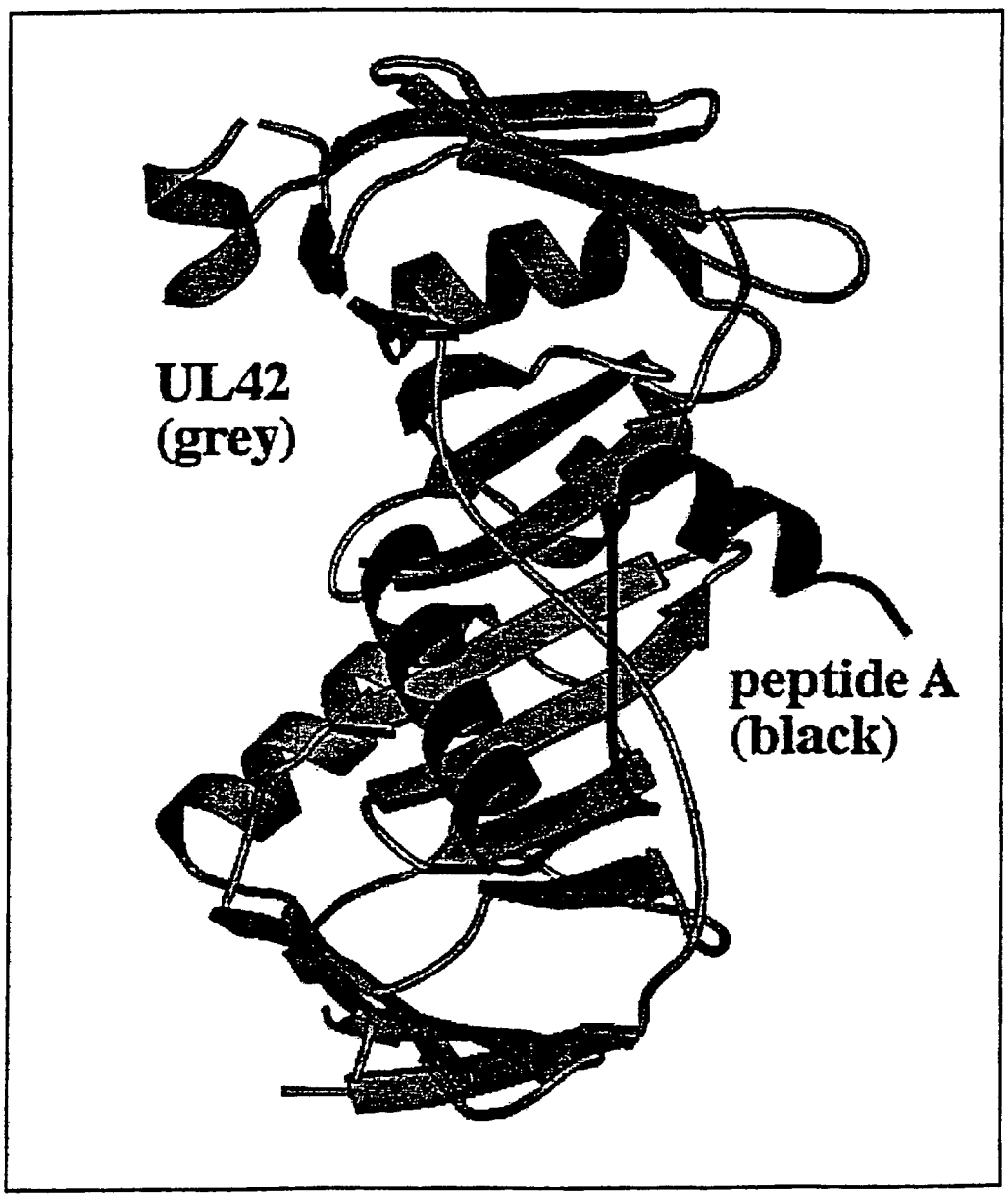
FIG. 2. Structure of UL42/peptide A complex solved to a resolution of 2.7 Å.

The instant invention encompasses the structure-based molecular design of inhibitors of processivity factor binding to proteins whose function is modified by interruption of the binding interaction between the protein and processivity factor subunits. Although the disruption of specific protein-protein interactions is a promising strategy for drug development, the nature of these interactions can make such disruption impractical. Many protein-protein interactions involve large surfaces or multiple contacts, making it unlikely that a single small molecule could interfere with them. In this regard, the instant inventors have identified particular binding sites in the polymerase/processivity factor interface.

"Processivity factor" as used herein is defined as a protein that modifies DNA polymerase to continuously incorporate many nucleotides using the same primer-template without dissociating from the template.

"Binding site" as used in the instant invention is any amino acid residue or residues of a protein, peptide or polypeptide which is involved in an attractive interaction with another residue or residues of a protein, peptide or polypeptide.

"Binding" as is used in the instant invention, refers to the attractive interaction between two or more molecules or between portions of two or more molecules.

"Spider" as used herein denotes a specific peptidomimetic framework that mimics the vectors between the beta carbons of the i, i+4, i+5 and i+7 residues of an alpha helix In one aspect of the instant invention, there is provided, a method for inhibiting processivity factor binding to protein. In overcoming the problems associated with the inhibition of protein-protein associations between DNA polymerase and processivity factors, the instant inventors have discovered particular and distinct binding sites on DNA polymerase and processivity factor. The particular binding sites are characterized as small and discrete to the degree that interruptions or non-conservative mutations at these sites will cause effective inhibition of processivity factor binding and will effect, for example, inhibition of long chain DNA synthesis in vitro. Moreover, the instant inventors have surprisingly and unexpectedly discovered the structural and topographical uniformity of processivity factors to effect inhibition of processivity factor/protein binding in for example, viral, bacterial, fungal and eukaryotic cells. Given these insights, such inhibition of processivity binding and inhibition of long chain DNA synthesis can be effected with an oligopeptide or a small molecule. The inhibitors can bind to sites on the polymerase or the processivity factor, or both.

The structure-based identification of relevant binding sites and inhibitors according to the instant invention involves: site-directed mutagenesis; peptide ligand display identification; structure-related studies of surrogate DNA polymerase C-terminus; Pol/ULA2 crystal structure; homology modeling of processivity factors from other viruses and other organisms.

Mapping a protein-protein interaction identifies particular amino acids within potential binding sites for drug action. The instant invention is based, in part, upon the identification of binding sites on DNA polymerase and processivity factor comprising specific amino acids. These binding sites have been particularly targeted for the introduction of mutations into the respective primary sequences. Comparative binding and DNA synthesis assays between the mutant polymerase and/or processivity factor and native/wild type proteins yield amino acid-specific data. These results particularly show potential binding sites.

Preferably, specific amino acid residues are pinpointed as sites for the introduction of mutations into the primary sequences. These amino acids are selected based upon their position such that if that amino acid residue position is modified, there will be a resultant alteration (i.e. decline) in the binding affinity.

Protein-protein interactions are often mediated by autonomous peptide motifs. By directing the assembly of specific protein complexes, such motifs can regulate diverse processes such as signal transduction, transcription and DNA replication. The present invention identifies specific binding sites within the C-terminal 36 residues of HSV polymerase (Pol), which are sufficient for interacting with a processivity subunit. As mentioned supra, since this interaction is required for viral replication, it is a potential target for antiviral drug discovery.

For example, functional mapping of Pol has indicated that the C-terminal amino acid residues are indicated for processivity factor binding (Stow, N. D. (1993) *Nucleic Acids Research* 21(1), 87-92; Digard et al., (1993) *J. Virol.* 67(1), 398-406; Marsden et al., (1994) *J. Gen. virol.* 75(Pt 11), 3127-3135; Tenney et al., (1993) *J. Virol.* 67(1), 543-547). This region of Pol is not highly conserved among any other cellular DNA polymerase. A polypeptide corresponding to the C-terminal 36 amino acid residues of Pol, designated Peptide A (FIG. 1, Pol residues 1200-1235) selectively inhibits the ability of UL42 to stimulate long chain DNA synthesis (Digard et al., (1995) *Proc. Natl. Acad. Sci. USA* 92, 1456-1460). Peptide A and a fusion peptide comprising to the last 18 residues of Pol bind specifically to UL42 indicating that this region of Pol is sufficient for UL42 binding (Loregian et al., (1996) *Protein Expression aMd Purification* 8, 381-389). A shorter peptide corresponding to the last 18 residues of Pol, designated as Peptide E (FIG. 1, Pol residues [1218-1235) also binds UL42 and is a specific inhibitor of UL42 function (Digard et al., (1995) *Proc. Natl. Acad. Sci. USA* 92, 1456-1460).

Peptide E, which corresponds to the C-terminal helix of peptide A, acts as a monomer and is only slightly less potent an inhibitor of long-chain DNA synthesis than peptide A. The binding of both peptides to UL42 as measured by isothermal titration calorimetry (ITC) correlates with their inhibitory activity, suggesting that inhibition in the polymerase assay does reflect a direct interaction with UL42. Because the C-terminal 18 residues of Pol appear to be most important for this interaction, structure-activity studies were done with variants of peptide E. Taken together with mutagenesis studies, the segment corresponding to residues 29-36 is a likely region for UL42 binding.

Surprisingly and unexpectedly, the region of Pol corresponding to peptide E is small and discrete, and therefore is a good target for site-irected mutagenesis studies. Mutations that most severely affected the inhibitory activity of this peptide occurred in two regions; at the N-terminus of the helix (T20A and E22A) and in the extreme C-terminus of the molecule (H29A, R30A and F32A). In the case of T20A and E22A mutants, which had lower helix content than the other peptides based on ellipticity at 222 nm., the mutations may simply alter the overall structure of the peptide. In contrast mutations in the extreme C-terminus of peptide E, including H29A and R30Ahad little effect on the degree of helicity, strongly suggesting that this region is directly involved in binding.

Mutational analyses of UIA2 (~25 deletion mutants and ~22 four-codon linker insertion mutants) identified a single insertion mutation at codon 160 that specifically impairs Pol-UL42 binding without affecting DNA binding. Several additional mutations just upstream of codon 160 did not drastically impair the Pol-UL42 interaction. However the closest insertion mutation downstream that we studied was at codon 191, leaving open the possibility that residues 160-190 include the subunit interface of UL42.

Mutagenesis is carried out using methods that are standard in the art, as described in, for example in *Current Protocols in Molecular Biology*, John Wiley & Sons, Inc., 1998. The mutated or variant Pol or processivity factor sequence is cloned into a DNA expression vector and is expressed in a suitable cell such as, for example, *E. coli*. Preferably, the DNA encoding the desired sequence is linked to a transcription regulatory element, and the variant is expressed as part of a fusion protein, for example, glutathione-5-transferase to facilitate purification. The variant protein is then purified using affinity chromatography or any other suitable method known in the art. "Purification" of polypeptide refers to the isolation of a protein or polypeptide in a form that allows its activity to be measured without interference by other components of the cell in which the polypeptide is expressed.

Using known peptide display technologies, peptides are identified that bind specifically to the C-terminus of Pol. Peptide libraries developed from this methodology fall into more than one sequence class, each of which could serve as starting points for the discovery of new inhibitors. In particular, one class of peptides had a consensus sequence QxxPxV, (where Q is glutamine, P is proline V is valine and x is any amino acid), and site directed mutagenesis confirmed that the Q in the motif was required for binding. Homology with a segment of UL42 corresponding to the binding residues of processivity factor strongly suggests that this segment interacts with Pol. Through routine design procedures a peptide based on one of the peptide display sequences can be designed, and screened. This information is important for structure-based design since alternative sequence classes serve as a basis for the discovery of new inhibitory agents.

Protein display is carried out by methods common in the art. For example, phage display involves expression of proteins and peptides on the surface of filamentous phage. A library of randomly mutated peptide DNAs are ligated to a phagemid vector, for example, M13-based phagemid vector, so that mutant peptide is fused to the carboxy terminal domain of the phage protein. The carboxy terminus of the phage protein associates with the phage particle and the amino terminus, containing protein mutants, is displayed on the outer surface of the phage. The library of phagernids is introduced into E. coli and then E coli. are then infected with helper phage that induces the production of phagemid particles. The mutant peptide-phage complexes are passed over a column containing ligand covalently linked to a substrate (i.e. beads). Only the tight binding peptides are retained and non binding peptide-phage mutants pass through the column. The bound phage are isolated, cultured in E. coli and passed over the column again. Repeated rounds of selection result in the identification of peptide variants that bind ligand with exceptionally high affinity.

Molecular modeling and protein homology modeling techniques can provide an understanding of the structure and activity of a given protein. The structural model of a protein can be determined directly from experimental data such as x-ray crystallography, indirectly by homology modeling or the like, or combinations thereof. Elucidation of the three-dimensional structure of the Pol-processivity factor complex provides a basis for the development of a rational drug design.

The structure of a complex of UL42 with peptide A has been solved to a resolution of 2.7 Å (FIG. 2). The nature of the UL42-Pol interactions together with the above information immediately suggest structure-based strategies and de novo design of combinatorial libraries of potential antivirals against HSV. Initial design focuses on peptide and peptide-like ligands that will compete with Pol for UL42 binding, or alternatively peptide or peptide-like ligands that compete with UL42 for Pol binding. The design focuses on specific interactions identified in the structure and particularly those interactions which were discovered by mutagenesis studies, e.g. Pol H1228 to UL42 R64 and Pol R1229 to UL42 Q171 (where H1228 and R1229 of Pol corresponds to H29 and R30 of Peptide A). In general, a library of compounds is generated that are capable of binding to key binding sites.

A general design strategy exploits the similarities among protein-processivity factor interactions. The strategy begins with the UL42-peptide A interaction as a target. The first step is molecular design with a central region capable of making extended interactions with the extended loop of UL42 and with additional groups at the end which bind to portions of the sites occupied by the terminal helices of peptide A. Alternatively, design libraries are made of molecules with a segment capable of making beta type interactions with the central portion of peptide A with additional functional groups to bind to specific sites on the terminal helices. The design is amenable to any of a number of existing or even novel combinatorial chemistries known in the art that produce libraries of peptide-like small molecules.

Libraries are screened by standard assays, for example, inhibition of long chain DNA synthesis or screening the ability of molecules to displace an easily detectable ligand from processivity factor or binding protein by, for example, radiolabeling or fluorescence labeling. The binding of screened compounds can be quantifiably characterized by isothermal calorimetry (ITC) which measures the heat given off by the ligand protein interaction and permits assessment of $K_d$, stoichiometry, and changes in enthalpy and entropy upon binding (Ladbury et al., *Chemistry & Biol.* 3, 791-801). This assay is used to screen mutant forms and potential ligand libraries against native processivity factor or the polymerase binding. Once a screened library is identified, it can be used as a structure-based "tool" for iterative modification and assay well within the skill of the artisan and the instant invention.

The instant invention encompasses the development of D-peptides useful for the inhibition of processivity factor binding to protein. This approach takes advantage of mirror-image relationships between naturally occurring L-peptides and unnatural D-peptides (Schumacher et al., 1996 *Science* 271, 1854-1857). Once tight binders have been identified, screened and selected, peptides comprising D-amino acid versions of them are synthesized. These D-peptides should then be tight binders of the natural L-Peptide A and inhibit protein-processivity factor interactions. As starting points for drug discovery, such peptides have a number of advantages over L-peptides, such as greater stability in vivo.

One route to drug discovery targeting the Pol-UL42 interaction is to identify peptides that mimic one interacting surface of the Pol-UL42 interaction and then, by altering each residue, develop non-peptide inhibitors (peptidornimetics). These compounds are often smaller than the original peptide and able to enter cells and inhibit the enzyme in situ.

Alpha helices are a critical portion of many protein-protein, protein-nucleic acid interfaces, and small helical peptides have been demonstrated to be capable of disrupting a number of macromolecular interactions. Therefore, small helical structures with appropriately chosen side chains might, in principle, serve as useful pharmacological agents. Unfortunately, with the exception of relatively small oligopeptides, the poor pharmacological properties of peptides (principally limited stability and limited ability to cross membranes) generally limit the utility of peptides as drugs. This problem is compounded for peptides bound as helices, since the smallest known stable helices contain at least seventeen residues (Marqusee et al., PNAS 86, 52865290, 1989).

One embodiment of the present invention is a class of synthetically accessible peptidomimetic framework, called "Spiders", amenable to solid phase synthesis and combinatorial methods, to mimic the vectors between the beta carbons of the i, i+4, i+5 and i+7 residues of an alpha helix. The framework displays four sidechains denoted $R^1, R^2, R^3$, and $R^4$. Charmm (Brooks et al., J. Comp. Chem. 4, 187-217, 1983; Karplus, M., CHARMM: Harvard College, 1992) calculations confirm that the minimum energy conformation of the Spider presents the sidechains in a position and orientation essentially equivalent to that of the four sidechains on one face of an alpha helix (i, i+1, i+4, i+5 or i, i+3, i+4, i+7 sidechains). No conformational dependence on the identity of the particular sidechains has been found. Spiders are much smaller than a comparable helix, which are believed to make them superior drug candidates, and they have fewer degrees of backbone freedom (5 vs. 16 for a typical helix) which is believed to reduce the energy penalty for binding.

Any biologically or pharmacologically relevant helix could be replaced by a corresponding Spider, making such Spiders attractive lead candidates for drug design and for target validation.

An illustrative synthetic scheme for preparing a Spider is shown below. Sidechains may correspond to the side chains of natural or unnatural amino acids. The stereochemistry of the $R^1$ and $R^4$ side chains could correspond to a D or an L amino acid, or (in the case of multiple stereo-centers) to any other stereochemistry. Combinatorial approaches (either split-and-pool synthesis or parallel synthesis) may be used to determine optimum sidechains. The Spiders have fewer degrees of freedom (5 in Spider backbone, vs. 16 for backbone of eight-residue helix). Consequently, entropy effects should favor the binding of Spiders over that of helices.

Solid Phase Synthesis of Spiders

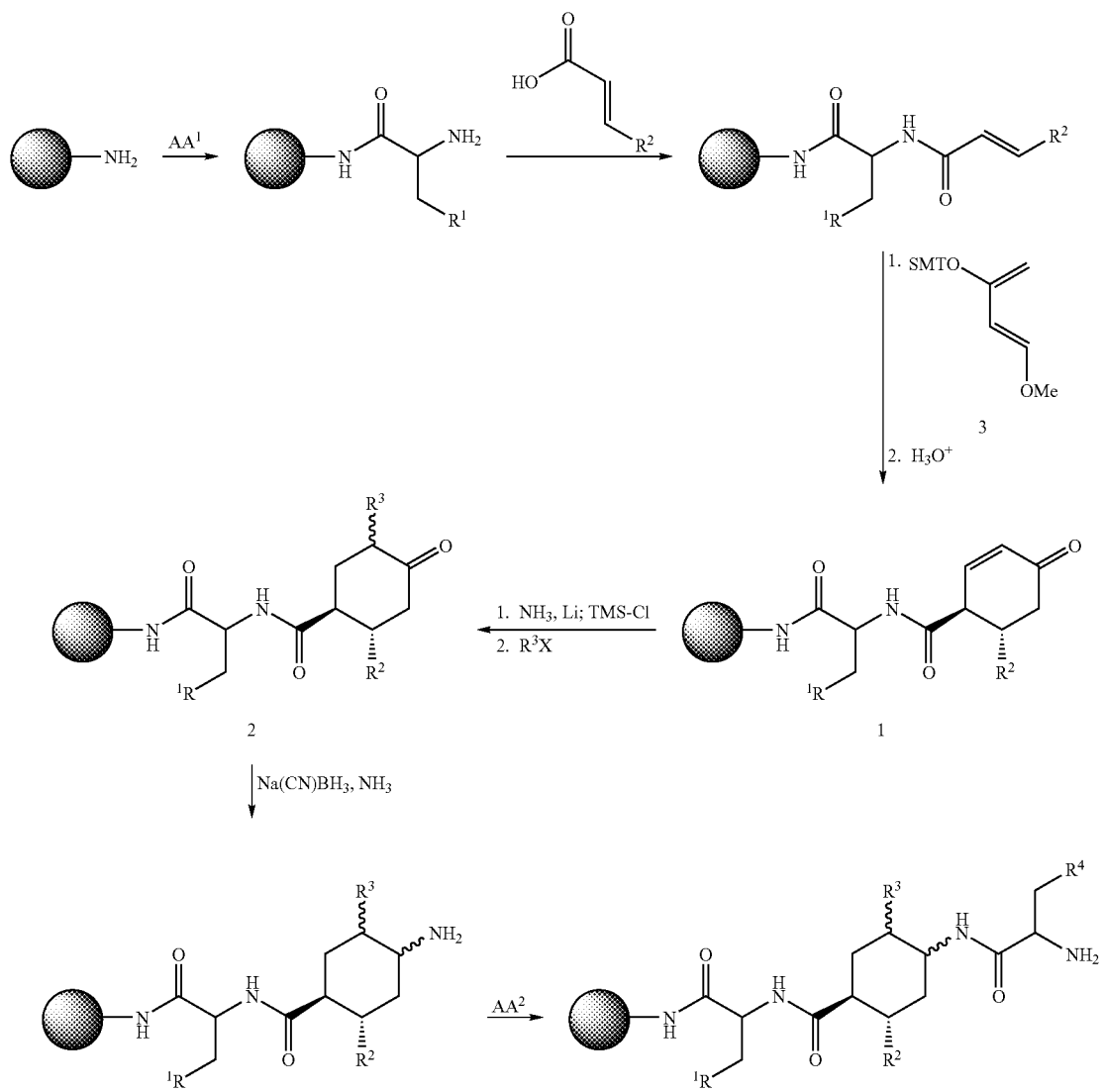

Three illustrative Spiders are shown, whose synthesis is achieved using standard methods, with the following sequences: EHNQ (SEQ ID NO: 1), WDHQ (SEQ ID NO: 2) and RDHO, where the $n^{th}$ letter is the 1-letter amino acid code for the side chain or side chain fragment attached to position $R_n$ of the Spider, (O stands for anthracine). All three spiders were selected in part using information provided by MCSS (Evensen et al., MCSS version 2.1, Cambridge, Mass.: Harvard University, 1997) calculations carried out on UL42 and mutagenesis experiments performed on Pol. The design protocol is given below. Each of the three spiders was designed to interact with UL42 and to sterically conflict with Pol, thus preventing it from binding to UL42.

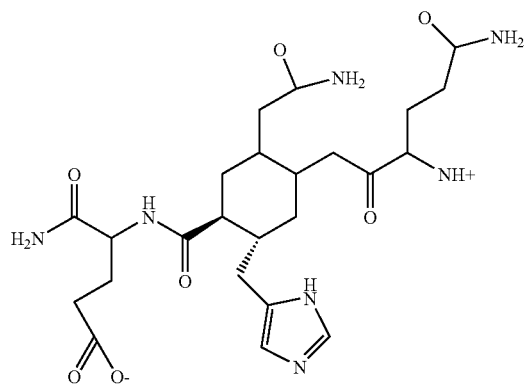

Spider WDHQ (SEQ ID NO: 2)

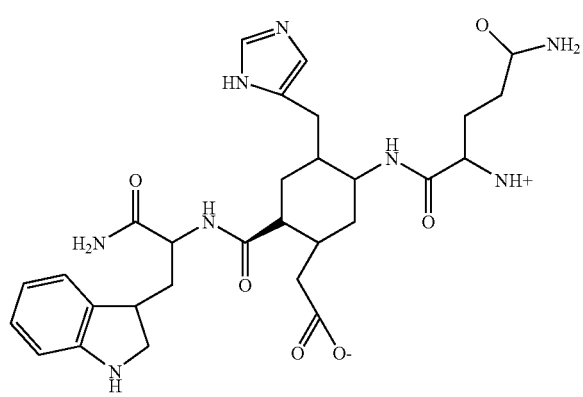

Charmm calculations (Brooks et al., J. Comp. Chem. 4, 187-217, 1983; Karplus, M., CHARMM: Harvard College, 1992) indicate that the interactions formed by Spider EHNQ (SEQ ID NO: 1) are primarily between polar or charged residues. The Glu (E) forms a salt-bridge with Arg 35 of UL42, (and can be closely superimposed on residue D1232 of the polymerase peptide). The H is (H) is positioned between Asp 34 and Arg 35, and interacts electrostatically with both. The positive region of the Asn (N) forms a polar interaction with Asp 34. The Gln (Q) interacts with Arg 35 and H is 54 of UL42.

The second Spider, WDHQ (SEQ ID NO: 2), was designed to interact with a hydrophobic region on the "floor" of the groove in which the peptide binds, which consists of Phe 49, Pro 51, Leu 52, Val 138, Pro 141, Ala 262, and Val 266, together with the backbones of other residues. The WDHQ (SEQ ID NO: 2) Spider was the best of several Spiders that have both hydrophobic residues designed to interact with the floor of the groove and hydrophilic residues to interact with nearby hydrophilic target residues. Charmm calculations (Brooks et al., J. Comp. Chem. 4, 187-217, 1983; Karplus, M., CHARMM: Harvard College, 1992) indicate that the Trp (W) interacts with Pro 51 and Leu 52. The Asp (D) forms a salt bridge to Arg 35, and the H is located in between Arg 35 and Glu 53, interacting with both. The Gln (Q) does not interact with UL42, but attempts to replace it with residues that do were not successful.

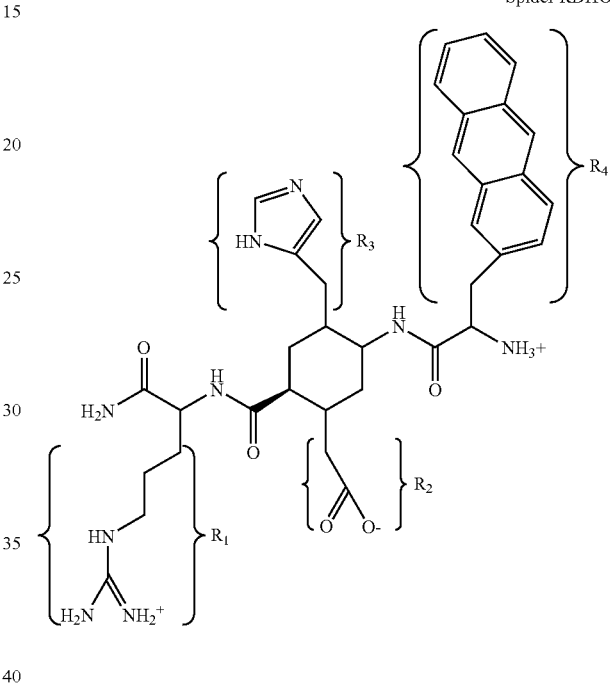

Spider RDHO

The Spider RDHO, with the O standing for anthracine, interacts with both the floor of the groove and with hydrophilic residues, and its design is similar to that of WDHQ (SEQ ID NO: 2). Charmm calculations (Brooks et al., J. Comp. Chem. 4, 187-217, 1983; Karplus, M., CHARMM: Harvard College, 1992) indicate that the anthracine forms hydrophobic contacts with Phe 49, Pro 51 and Pro 141 (which is along the side of the groove). The D forms a salt bridge with Lys 243, and the H makes the same interactions as the H in Spider WDHQ (SEQ ID NO: 2). The Arg (R) does not specifically interact with any residue in UL42.

Although the above synthesis depicts a serial synthesis in which the central 1-amino-4-carboxycyclohexane moiety is constructed on a growing peptide chain, it will be appreciated that libraries may be assembled in which the 2,5-disubstituted-1-amino-4-carboxycylcohexane units are synthesized separately and treated as pseudopeptide monomers in standard automated peptide synthesis. Multiple 2,5-disubstituted-1-amino-4-carboxycyclohexanes may also be coupled sequentially. This can mimic a larger helix. Combinatorial approaches can also be used on such larger molecules. A few illustrative Spiders with larger structures are shown below.

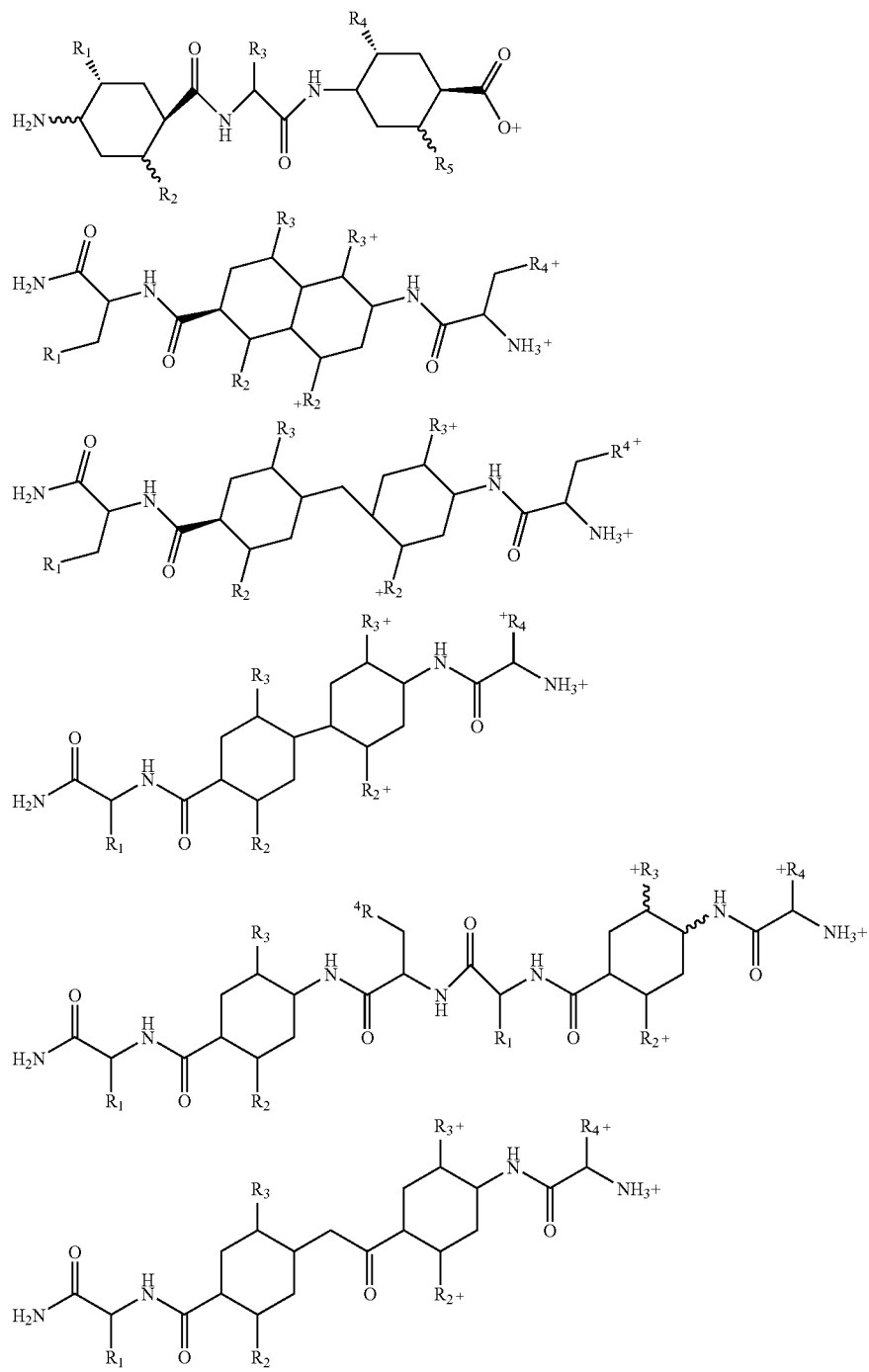

It will be apparent to the ordinary skilled artisan that many other variants are possible that also provide the required stereochemical relationship of amino acid side chain fragments to mimic both helical and non-helical portions of either the polymerase or the processivity factor component of a complementary pair necessary for DNA expression or repair. In the above illustration for peptidomimetics of helical structures, it will be apparent that the cyclohexane rings can be replaced by other homocyclic or heterocyclic alicyclic or aromatic rings of various sizes and shapes, including fused and bridged ring systems. By the same token, the linkage between rings can be direct, or through intermediate linker moieties, including those comprising peptide bonds to facilitate solid phase synthesis. Existing combinatorial chemical techniques can be used to select appropriate rigid scaffolds to achieve the spatial and conformational orientation of functional groups to interact with groups on the polymerase or processivity factor and inhibit binding of the two complementary proteins. It will be appreciated also that amino acid side chain functional groups can be replaced by analogues having similar functionality, e.g., sulfonate, phosphate for carboxylate; sulfhydryl for hydroxyl; urea, carbamate, urethane for guanidine; and the like. Several atoms in a side chain can be incorporated into rings or other mimetic fragments in a similar fashion to the illustrated groups above. In appropriate cases, this provides further rigidity and fewer degrees of freedom to the system.

Computational Methods

There are many successful techniques for determining the optimum binding position and orientation for a small molecule of known structure (the "docking problem"). Techniques also exist for determining the optimum sidechains. These include dead-end elimination of a molecule with a particular binding conformation. See, e.g., Dahiyat et al., Protein Sci 6, 1333-7, 1997; Lasters et al., Protein Eng 6, 717-22, 1993. The present inventors use a novel methodology to determine optimum sidechains for their peptidomimetic scaffold along with its optimum position and orientation.

The distribution of conformations of macromolecules in equilibrium constitutes a canonical ensemble. In this state, the lowest energy minima will be the most populated, and larger energy gaps will lead to a larger portion of the population being similar to the lowest energy conformation. Conversely, the distribution of conformations themselves can be used to determine the energy gap of a molecule. Studies, e.g., DeWitte et al., JACS 118, 11733-11744, 1996; Finkelstein et al., 1993). FEBS 325, 23-28, 1993, have argued that the principles of canonical statistical mechanics can be applied to subsets of folded proteins because the subsets are in thermal equilibrium with each other. For similar reasons, the present inventors have found that the principles of canonical statistical mechanics can be applied to ligand sidechains, provided that the ligand remains bound to its target significantly longer than the time scales of the thermal fluctuations of the system.

Multiple (typically 150) simulated annealing dynamics calculations, each using a different random number seed, are carried out using Charmm (Brooks et al., 1983; Karplus, 1992). Sidechains that have a small positional variance are likely to be making large energetic contributions to binding, while those with a large positional variance are less likely to be making energy contributions to binding. The sidechain with the greatest positional variance is changed to another sidechain; the replacement sidechain is selected on the basis of stereochemical intuition, Monte-Carlo criteria or other methods. The entire process is repeated until convergence is achieved.

It is necessary to resort to indirect measurement of the energy contributions of sidechains because binding is often largely driven by enhanced intra-molecular binding due to solvent screening, and so direct measurement of sidechain energy contributions is often difficult or misleading. See, e.g., Hendsch et al., Protein Science 8, 1381-1392, 1999.

Based upon the structure of peptide and non-peptide lead compounds, it is well within the skill of the ordinary artisan to develop non-peptide small molecule inhibitors for example, with the use of a computer to put different functional groups together yielding small molecules that bind tightly. The success of a structure-based drug design method is then enhanced through the use of advanced methods of computation. These methods expedite the identification of key molecular fragments which then are joined to form larger fragment molecules (LUDI: Bohm, H. J. (1992) *J. Comput. Aid. Mol. Des.* 6: 61-78; MCSS: Miranker, A. and Karplus, M. (1991) *Proteins* 11: 29-34; GRID: Goodford, P. J. (1985) *J. Med. Chem.* 28:849-85) or whole molecules either from a database of existing compounds or through a molecular growth algorithm (DOCK Kuntz et al., 1992 *Science* 257, 1078-1082; Kuntz et al., 1982 *J. Mol. Biol.* 161, 269-288). These computational advances enhance the ability to develop molecules or ligands which will successfully bind to protein sites. An iterative cycle is conducted of solving structures of new compounds and assay, permitting the design of better candidate inhibitors. Compounds which bind are rescreened for ability to inhibit a biochemical process (e.g., processive DNA synthesis in vitro) or biological process (e.g., virus replication in vivo) to identify viable drug candidates.

There is provided, in one aspect of the invention, methods for treating infections effected by viruses, bacteria, and fungi. Despite the disparate mechanisms and lack of sequence homology, UL42 bears a striking structural homology with other sliding clamps as shown in FIG. 3. Stereoviews of processivity factors in FIG. 4 also show a common topology. Moreover, the nature of the ULA2-Peptide A interaction bears a striking similarity with the interaction of processivity factor RB69 gp45 with a RB69 Pol-derived peptide and the interaction of human processivity factor PCNA with a peptide derived from cell cycle regulator, p21. In the UL42-Peptide A complex and the PCNA-p21 peptide complex, the peptides form a short stretch of beta interactions with a portion of a loop that connects the bottom half and top half of the processivity factor. In all cases the peptides bury an aromatic side chain in a conserved hydrophobic pocket near the carboxy terminal end of the connecting loop in the processivity factor. The crystal structure of the UL42-Peptide A complex does in fact indicate that specific contacts are made between UL42 and the C-terminal helix of Peptide A, including one with the side chain of arginine 30 (which corresponds to R1229 in the intact polymerase).

To go from the specific case of UL42-Pol interactions to other targets, use is made of the similarities between the UL42-peptide A structure and the sliding clamp-peptide structures. As shown in FIGS. 2 and 3, the structure of processivity factor PCNA has been solved alone and as a complex with a peptide fragment from the regulatory protein p21. The p21 peptide interacts with a face of the PCNA molecule that can be thought of as a twisted surface comprised of beta sheets which is crossed by a long extended stretch of residues called the connecting loop. The structure, of a second clamp-like processivity factor, the gp45 protein from the phage RB69 has been solved alone and in complex with a peptide corresponding to the extreme C-termiinus of the phage polymerase. The structure of the gp45 trimer is strikingly similar to the PCNA clamp (FIG. 4). The C-terminal peptide from the phage polymerase interacts with a face of the gp45 protein that is homologous to the p21 binding face in PCNA. However, there have been no reported studies done of particular binding sites important for binding between gp45 and phage polymerase.

The strong similarities between the interactions in the known processivity factor peptide complexes puts it well within the skill of the artisan that this structure-based strategy may be quite general for other polymerases including bacterial, fungal and eukaryotic polymerases. Indeed, it is not necessary to solve the structure of a new processivity factor or peptide-processivity factor complex in order to derive a template for combinatorial libraries. Instead it is sufficient to derive a structure-based sequence alignment and a profile that allows the sequence of a processivity factor of unknown structure to be threaded into the framework of the known structure. These provide sufficient information to establish combinatorial libraries supra. This approach is quite general, allowing the design of inhibitors of processivity factor-Pol interactions for any polymerase which are candidate antivirals against a number of DNA viruses (e.g. herpesviruses, poxviruses), and the design of antimicrobials against pathogenic bacteria, pathogenic protozoans, and pathogenic fungi. Additionally, given the interactions of PCNA with a cell cycle regulatory protein and the interactions of repair proteins similar to sliding clamps with other proteins, this approach will be useful in cancer chemotherapy.

Although, the instant invention is drawn to the inhibition of interactions between processivity factor and protein in general, particular proteins are known to have functional modification or change effected by processivity factor binding, for example, restriction repair enzymes or cell cycle regulators. As such, other proteins that interact with processivity factors are within the knowledge of one of ordinary skill and therefore, well within the scope of the instant invention.

Because there are recognizable sequence homologies between UL42 and the processivity factors of the alpha herpesviruses (e.g., HSV-1, HSV-2, Varicella zoster virus and pseudorabies virus), the derivation of homology models for the processivity factors of the alpha-herpes viruses will be straightforward. Similarly, significant sequence homologies among eukaryotic PCNA's should allow relatively straightforward derivation of homology models for the eukaryotic processivity factors. Protein homology modeling requires the alignment of the protein under study with a second protein whose crystal structure is known. Information gained from these structure sequence alignments together with structure alignments of the processivity factors that have experimentally derived structures are used to derive a profile that will allow homology modeling and even identification of other processivity factors and target binding sites.

For example, a standard method for structure-based modeling adapted to this invention comprises modeling a target processivity factor based on a template selected from experimentally derived processivity factor structures, wherein the modeling comprises:(i) aligning the primary sequence of the target processivity factor sequence on the sequence of the template by pair-wise, structure-based or multiple sequence alignment to achieve a maximal homology score followed by repositioning gaps to conserve regular secondary structures; (ii) transposing the aligned sequence to the three dimensional structure of the template to derive the three-dimensional structure of the target processivity factor; (iii) subjecting the structure obtained in step (ii) to energy minimization; and (iv) identifying binding sites in the model based upon corresponding binding sites from the experimentally derived processivity factor structures.

Where standard sequence alignment tools fail to recognize sequence homologies between UL42 and other known non-herpes processivity factors (including the processivity factors of the beta and gamma herpesviruses), secondary structure-based predictions to match proteins are able to detect a significant relationship between UL42 and known processivity factor structures. In this regard, it is useful to note that, whereas standard sequence alignment tools fail to recognize sequence homologies between UL42 and other known non-herpes processivity factors, computer-based tools that use secondary structure predictions to match proteins, for example, (http://fold.doe-mbi.ucla.edulHome) was able to detect a significant relationship between UL42 and PCNA.

As such, a structure-based method for designing potential inhibitors of a DNA polymerase comprises modeling a target processivity factor based on a template selected from experimentally derived processivity factor structures, wherein said modeling comprises: using computer-based tools predicting secondary structure in said target based upon secondary structure in said template to provide a three dimensional model of said target; and identifying binding sites in said model based upon corresponding binding sites from said template.

Inclusion of the structures of all four processivity factors whose structures are known (PCNA, the $E.\ coli$ β subunit, gp45 and UL42) and the sequences of all known members of each of the families represented by the three structures, enables one of ordinary skill to significantly expand the ability to generate homology based structures and structure-based inhibitors of processivity binding to other polymerases, for example, eukaryotic, fungal and bacterial.

In another aspect of the instant invention, there are provided methods for treating cancer or inhibiting tumor growth. Cancer, as is used in the instant invention, refers to any abnormal new growths of tissue. There are two ways in which the instant invention can lead to therapies for treating cancer. Cancer cells are usually characterized by having fewer controls on the replication of their DNA than do normal cells. Thus, inhibition of DNA synthesis is well established as a mechanism for selectively inhibiting tumor cells. Inhibiting the interactions between cellular DNA polymerases such as DNA polymerase delta with their processivity factors, e.g. PCNA, is one approach to inhibit tumor cell replication. A second strategy would be to block the interaction of p21 or other regulatory proteins with PCNA or other processivity factors. In the absence of other regulatory pathways, which would be more likely to be missing in cancer cells than in other cells, this approach drives cancer cells into unscheduled DNA replication, leading to cell death, perhaps in combination with other agents that would, for example, be incorporated into replicating DNA. Once compounds are screened for inhibitory activity as described, assays are carried out for anti-cancer activity such as tumor cell death in vitro, or by measuring, for example, tumor growth or tumor weight in vivo in a suitable model such as a rat or mouse.

Based on the description supra it will readily be appreciated by those of ordinary skill in the art that the instant invention can be used for design of agents that block interaction of HSV Pol and UL42 as antivirals against HSV-1 and HSV-2 and the design of agents that block Pol/processivity factor interactions in other alphaherpes viruses that cause disease in humans including varicella zoster, and monkey herpesvirus B as antivirals.

The instant invention can also be used for the particular design of agents that block Pol/processivity factor interactions in other human herpes viruses including the beta herpes viruses such as CMV, HHV6 and HHV7 and the gamma herpes viruses such as Epstein-Barr Virus and HHV8 as antivirals.

The instant invention can also be used for the particular design of agents that block Pol/processivity factor interactions in beta-herpesviruses that cause viral infection in animals e.g. pseudorabies virus, equine herpesviruses, bovine herpesviruses as veterinary antivirals, design of agents that block polymerase/processivity factors in any other DNA virus that encodes its own polymerase and processivity factor (e.g. variola) as antivirals, design of agents that block Pol/processivity factors of pathogenic bacteria as specific antibacterials, design of agents that block Pol/processivity factor interactions in pathogenic fungi as antifingals, design of agents that block Pol/processivity factor interactions in pathogenic protozoans as antiprotozoans, design of agents that block processivity factor-protein interactions in cancer cells as anti-tumor drugs or drugs that potentiate the action of other anti-tumor drugs.

The present invention, thus generally described, will be understood more readily by reference to the following examples, which are provided by way of illustration and are not intended to be limiting of the present invention.

Materials

Peptide A and its variants were synthesized as described previously (Digard et al., 1995 *Proc. Natl. Acad. Sci. USA* 92, 1456-1460). Alanine scan mutants of peptide E. HSV Pol and UL42 were purified from insect cells infected with the appropriate recombinant baculoviruses as described previously (Gottlieb et al., 1990 *J. Virol.* 64, 5976-5987; Marcy et al., 1990 *Nucleic Acids Res.* 18(5), 1207-1215. Poly(dA) template and oligo(dT) primer were purchased from Pharmacia. TTP (thymidine triphosphate) was purchased from Boehringer Mannheim and [$^{32}$P]-TTP was obtained from DuPont NEN.

Site-Directed Mutagenesis Mapping on Peotide E

To address the contributions of various residues to the interaction, peptides were synthesized in which each of the non-alanine residues in peptide E was substituted with alanine (Ala) to try to maintain helicity, but change sequence. These peptides were tested for their effects on UL42-mediated long chain synthesis. TABLE 1 indicates two clusters of substitutions that eliminated detectable inhibitor activity; one cluster near the N-terminus of the peptide and the other near the C-terminus (the M27A mutant inhibited long chain synthesis by about 40% at 100 µM). The N-terminal substitutions reduced helicity as measured by ellipticity at 222 nm.

TABLE 1 also shows that protein-protein mapping indicates residues in the C-terminus such as H29, R30 and F32 may be indicated for the interaction with UL42 and indeed may directly participate in this interaction. This also indicates that a small molecule could also exert drastic effects on the Pol-UL42 interaction at these sites.

TABLE 1

Inhibition of long chain DNA synthesis by peptide E mutants. The $IC_{50}$ values (concentrations of peptides that give 50% inhibition) ± standard deviation of the various peptide E mutants and the % helicity calculated from ellipticity values at 222 nm from CD measurements. Assays performed essentially as described (Digard et al., 1995). The mutants are named relative to the peptide A sequence with the first letter and number = wt residue number; A = alanine.

| Peptide | $IC_{50}$ (µM) | % Helicity |
|---|---|---|
| A | 1.7 ± 1 | 20 |
| E | 11 ± 5 | 25 |
| T20A | >100 | 16 |
| E22A | >100 | 14 |
| E23A | 21 ± 8 | |
| T24A | 77 ± 30 | |
| R25A | 40 ± 13 | |
| R26A | 14 ± 9 | |
| M27A | >100 | |
| L28A | 18 ± 6 | |
| H29A | >100 | 25 |
| R30A | >100 | 26 |
| F32A | >100 | 28 |
| D33A | 50 ± 13 | |
| T34A | 10 ± 5 | |
| L35A | 97 ± 5 | |

Identification of Specific Residues of Peptide E for Inhibitory Activity

Figure 5:
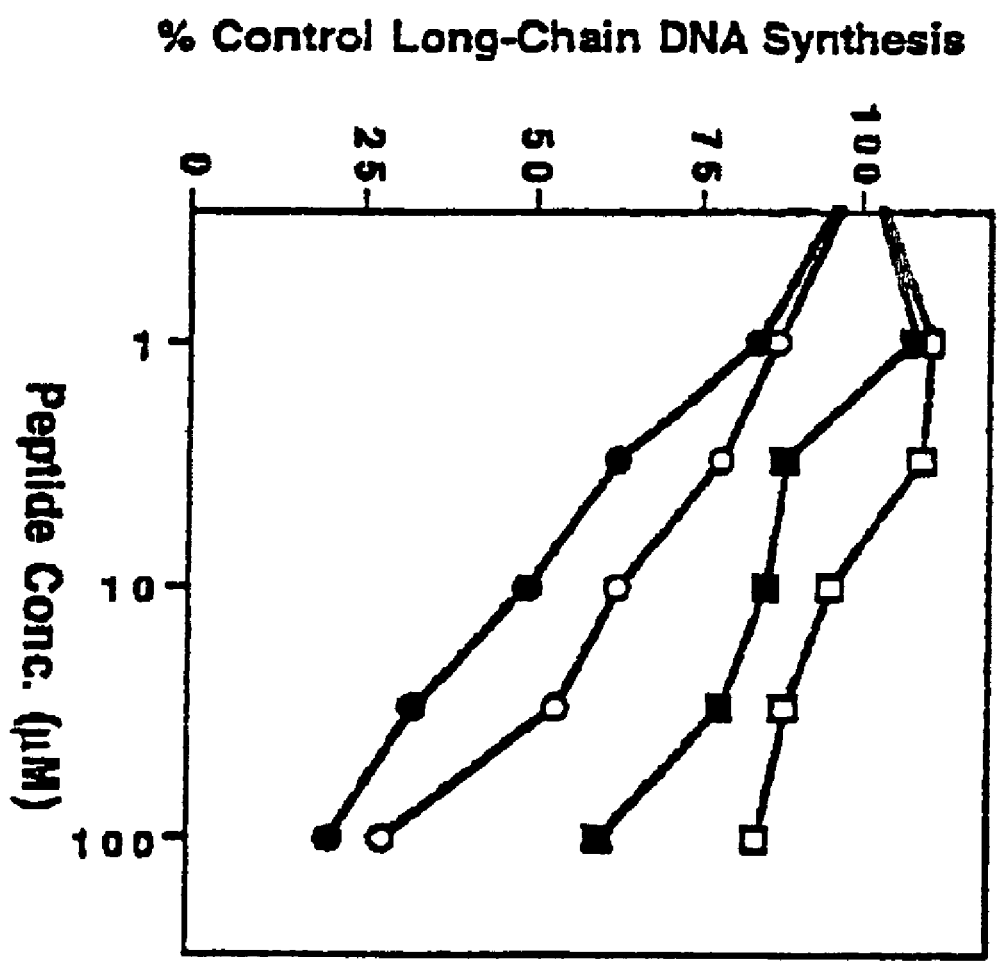
FIG. 5. Concentration-response curves of peptide E mutant inhibition of long-chain DNA synthesis. •-peptide E, O—R25A, ■-M27A, □-R30A FIG. 6. CD spectra of peptide E mutants.

To perform structure-activity studies, "alanine scan" mutants of peptide E, in which each non-alanine residue was individually converted to an alanine, were synthesized and tested for their ability to inhibit long-chain DNA synthesis by Pol and UTL42. A poly(dA)/oligo(dT$_{15}$) template/primer was employed. On this primer/template, Pol alone adds only one or two bases, but when UL42 is present, longer DNA products are formed. DNA products greater than 18 bases were quantified at varying peptide concentrations and expressed as a percentage of products formed by Pol/UL42 in the presence of vehicle control. These values were used to generate concentration-response curves, examples of which are shown in FIG. 5. As summarized in TABLE 1, mutants E23A, R26A, L28A and T34A, numbered relative to the peptide A sequence, had activities similar to that of peptide E. Mutants T24A, R25A and D33A were only moderately impaired in their ability to inhibit processivity with $IC_{50}$ values 3 to 7-fold greater than that of peptide E. Mutants L35A and M27A had even less activity exhibiting 50% and 40% inhibition at 100 µM respectively (data not shown). The most impaired mutants were T20A, E22A, H29A, R30A and F32A, which exhibited less than 20% inhibition at 100 µM. None of the peptide mutants inhibited Pol catalytic activity in the absence of UL42, demonstrating their specificity for UL42-mediated DNA synthesis.

Figure 6:
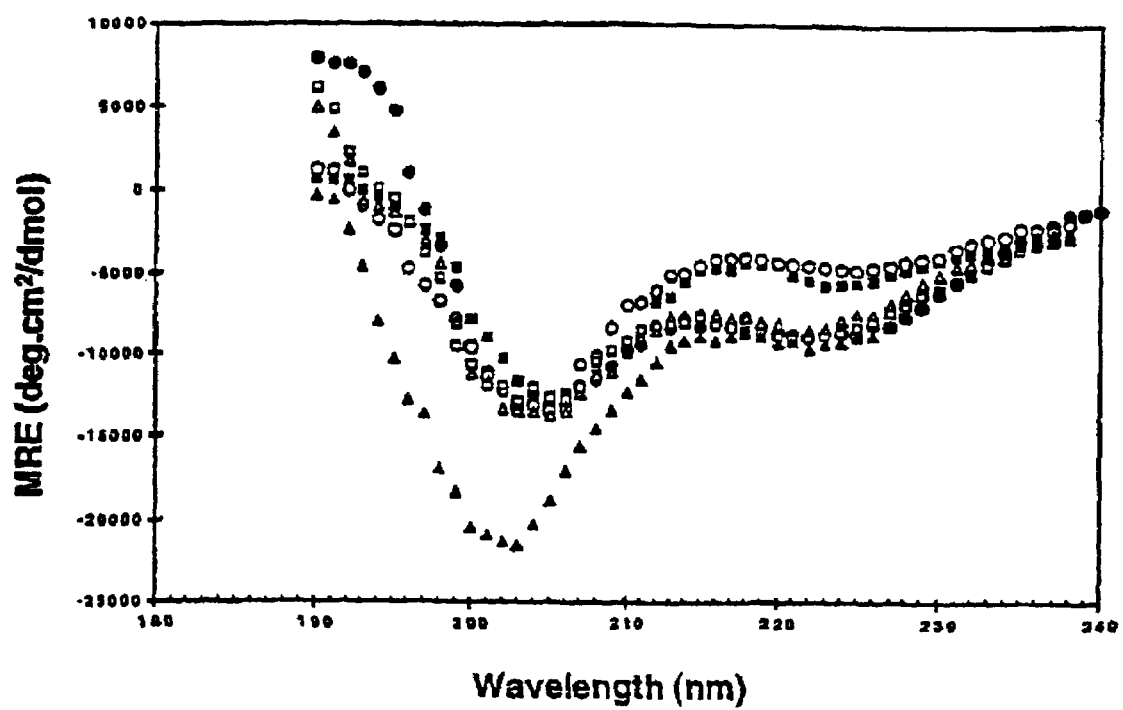

CD spectroscopy was performed in order to determine if the peptides with the least inhibitory activity were altered structurally. As shown in FIG. 6, wavelength scans of the mutants were characteristic of helical peptides with minima at 222 and 205 nm and a maximum at 190. Mutants T20A and E22A had substantially lower ellipticity at 222 mm than the other peptides, suggesting a loss of helical content. Therefore, the lack of inhibitory activity of these two mutants may be at least in part due to alterations in structure. Although the mutant F32A had a minimum at 222 nm similar to that of peptide E, it had a much deeper minimum at 205 nm, perhaps signifying a loss of helicity in this peptide as well. The CD spectra of the H29A and R30A mutants were nearly indistinguishable from that of peptide E suggesting that these residues may be directly involved in binding.

CD Spectroscopy

Lyophilized peptides were resuspended in 10 mM KF and adjusted to pH 8 with KOH. Spectra were recorded at the indicated peptide concentrations with an Aviv 62DS SpectroPolarimeter at 0° C. in a 0.1 cm pathlength cuvette. Wavelength scans were recorded at 1 nm intervals with a 5 second averaging time, and 5 to 10 scans were averaged. Peptide concentrations were determined by quantitative amino acid analysis. Unfolding curves were obtained by monitoring mean residue ellipticity at 222 nm as a function of the concentration of guanidine-HCl and temperature. These experiments employed an automated titrator as suggested by the vendor.

Site-Directed Mutagenesis Mapping on UL42

Mutant maltose binding protein (MBP)-UL42 fusion proteins were constructed with alterations in the consensus residues identified by peptide display. For example, glutamine 171 was altered. The mutant protein did not support long chain synthesis by Pol. It did not interact with peptide A in ITC assays, although it retained the ability to bind DNA. Thus, this segment of UL42 is specifically crucial for Pol binding. This supports the idea that this segment forms at least part of the Pol-binding site, which will provide a starting point for finding peptides and eventually peptidomimetics that can bind to Pol and inhibit viral replication. It also can abet structure-based design.

Peptide Display Identification of Ligands

Peptide ligands that could bind to GST-peptide A, but not to GST alone were selected, using phage display and *E. coli* flagellar display (valencies of 5-10 peptides), eluting bound ligands with UL42 or NaCl. A number of classes of peptides were identified. Each of these classes could serve as a starting point for drug discovery. Both display methods selected peptide sequences that align with the region of UL42 downstream of residue 160, specifically residues 171-176 (FIG. 7). This indicates that residues 171-176 form at least a portion of the Pol-binding site on UL42.

Polymerase Assays

Reaction mixtures contained 50 mM Tris-Cl (pH 7.6), 100 mM $(NH_4)_2SO_4$, 3 mM $MgCl_2$, 0.1 mM EDTA, 1 mM dithiothreitol, 0.1 µg BSA, 4% glycerol, 0.25 µg of poly(dA)-oligo (dT) primer/template, 50CM [$^{32}$P]-TTP (5 Ci/mMol), 100 fmol of HSV Pol, 200 fmol of UL42 and varying concentrations of peptide inhibitors in a final volume of 25 µL. Reactions were carried out at 37° C. for 5 to 10 minutes. Reactions were stopped by placing them on ice and adding 5 µL of alkaline loading buffer (2 mM EDTA, 50 mM NaOH, 2.5% glycerol, 0.025% bromcresol green) and were then loaded onto a 4% alkaline agarose gel. Gels were dried overnight and used to expose film and phosphoresence screens. Because Pol alone added only 1-2 nucleotides to the 15 base primer, newly synthesized DNA larger than 18 bases was defined as long-chain and quantified using a Molecular Dynamics Phosphorimager.

Pol/UL42 Crystal Structure

Protein Purification

UL42ΔC320 (a construct truncated at residue 320 to delete a proline-rich domain) was expressed as a fusion protein to maltose binding protein (MBP), and Peptide A was expressed as a fusion protein to glutathione-5-transferase (GST). Both proteins contained a PRESCISSION™ protease site between the protein of interest and the fusion partner. The proteins were expressed in *E. coli* strain BL21(DE3)$_p$LysS. Typically 8 liters of cells (6 L of MBPUL42ΔC320 and 2 L of GSTpeptideA) were grown in LB media containing 2% glucose and 100 µg/mL of ampicillin. The cells were grown to an O.D. 600 nm of between 0.6-0.8, and then induced for 5 hours by the addition of 3mL of 100 mM IPTG. The cells containing each protein were combined and pelleted at 3000×g. The pelleted cells were resuspended in 50 mM TRIS pH 7.5, 500 mM NaCl, 10 mM EDTA, 2 mM dithiothreitol (DTT) and 1% Triton X-100, and stored at –20° C. until needed.

The cells were thawed and lysed by sonication. The lysate was centrifuged at 10,000×g for 20 minutes and applied to a 10 mL glutathione Sepharose column that had been equilibrated with 50 mM TRIS pH 7.5, 500 mM NaCl, 5 mM EDTA, and 2 mM DTT. The column washed with approximately 50 mL of equilibration buffer, followed by a wash with 50 mM TRIS pH 7.5, 150 mM NaCl, 5 mM EDTA and 2 mM DTT until the absorbance at 280 nM had returned to baseline. The bound proteins were eluted off the column with 100 mM TRIS pH 7.5, 150 mM NaCl, 5 mM EDTA, 2 mM DTT and 15 mM reduced glutathione. The fractions containing the protein as judged by the UV absorbance at 280 nm, were pooled and PRESCISSION™ protease was added. The sample was dialyzed overnight against 50 mM TRIS pH 7.5, 150 mM NaCl, and 2 mM DTT. The sample was next desalted in a Centriprep 10 (Millipore) concentrator using a buffer of 50 mM HEPES pH 7.5, 2 mM DTT. The desalted mixture was applied to a single stranded DNA agarose column that had been equilibrated in 50 mM HEPES pH 7.5, 2 mM DTT. The bound protein was washed with 50 mL of 50 mM HEPES pH 7.5, 100 mM NaCl and 2 mM DTT.

The bound complex of UL42ΔC320/peptide A was eluted off the column using 50 mM HEPES pH 7.5, 2 mM DTT and 750 mM NaCl. The protein was then desalted in a Centriprep 10 concentrator using 50 mM TRIS pH 8.5, 2 mM DTT. The desalted protein was applied to a 5 mL Fast Q-Sepharose column equilibrated with 50 mM TRIS pH 8.5, 2 mM DTT. The protein was eluted off using a linear salt gradient from 50 to 600 mM NaCl. The purified complex was then dialyzed overnight against 50 mM TRIS pH 7.5, 150 mM NaCl, 2 mM DTT.

Preparation of Selenomethione UL42ΔC320/Peptide A

Selenomethionine UL42ΔC320 was prepared by the overexpression of the protein in *E. coli* strain BL21(DE3)pLysS in M9 minimal media containing 2% glucose and 100 µg/mL of ampicillin. Once cells reached an O.D. at 600 nM of 0.8-1.0 methionine biosynthesis was down regulated by the addition of isoleucine, leucine, lysine, phenylalanine, threonine, and valine. Fifteen minutes after the addition of the supplemental amino acids, the cells were induced for 5 hours by the addition of 3 mL of 100 mM IPTG. Cells were pelleted at 3000×g and resuspended in 50 mM TRIS pH 7.5, 500 mM NaCl, 10 mM EDTA, 2 mM dithiothreitol (DTT) and 1% Triton X-100, and stored at –20° C. until needed.

Subsequently the cells were thawed and combined with cells containing GST-Peptide A that were grown as described in the above section. The combined cells were lysed, and the complex purified as described above.

Crystallization

The purified protein was concentrated to 7-10 mg/mL as judged by Bradford assay. The concentrated protein was crystallized by the vapor diffusion method using 14-10% polyethylene glycol monomethyl ether 5000 as the precipitant. 2 µs of complex were mixed with 2 µl of reservoir solution on a siliconized coverslip and then inverted over the reservoir solution. Crystals usually appeared within 1-3 days. Crystals belonged to spacegroup P2, with unit cell dimensions a=54.3 b=100.6 c=129.5 Å and β=100.6°. There are four molecules of the UL42/Peptide A complex in the asymmetric unit. The native Patterson gave a strong peak at approximately ½, 0, ½ suggesting a pseudocentering operation.

The coverslips containing the crystals were inverted and cryosolvent (reservoir solution containing 20% glycerol, 25 mM TRIS pH 7.5, and 125 mM NaCl) was added until no further mixing was observed. The crystals were mounted in nylon loops and frozen directly in the nitrogen stream. Crystals used at CHESS (Cornell High Energy Synchrotron Source) were stored in liquid nitrogen until the time of data collection.

Heavy atom derivatives were made by soaking the crystals in reservoir solution contain 1 mM of the heavy atom compound either ethylmercury phosphate (EMP) or trimethyl lead acetate (TMLA) for between 12 and 24 hours, and mounted in nylon loops as stated above.

Data from all the crystals were processed using DENZO and SCALEPACK (Otwinowski, 1993, Data Collection and Processing, L. Sawyer, N. Isaacs and S. Bailey, eds. (SERC Daresbury Laboratory, Warrington, pp. 56-62). Structure factors from both data sets were calculated using TRUNCATE, and the derivative, native and selenomethionine data sets were scaled using SCALEIT (CCP4, Bailey, 1994, Acta Cryst. D50, 760-763).

Structure Determination

The positions of the lead and mercury sites were determined using conventional Patterson methods and difference Fouriers. The selenomethionine sites were found using anomalous difference Fouriers using the combined phases from the mercury and lead derivatives. The position of the heavy atom sites were refined using SHARP (Fortelle et al., 1997, SHARP: A maximum likelihood heavy-atom parameter refinement and phasing program for the MIR and MAD methods, Volume 7, P. Bourne and K. Watenpaugh, eds.) and initial MIRAS (multiple isomorphous replacement with anomalous scattering) phases were calculated. The data was then subjected to solvent flipping using SOLOMON (Abrahams and Leslie, 1996, Acta. Cryst. D52, 3042). The position of the heavy atom sites allowed the definition of the noncrystallographic symmetry (NCS) operators. Four fold NCS averaging greatly improved the quality of the experimental phases and allowed the initial tracing of the chain using the program 0 (Jones et al., 1990, Acta Cryst. A47, 110-119).

The structure was refined using CNSv0.5 (Brünger, 1992, *A System for X-ray Crystallograph and NMR*, New Haven: Yale University Press); Brünger et al., 1998, Acta Cryst. D54, 905-921). Rounds of energy minimization, followed by simulated annealing and B-factor refinement were carried out with rebuilding of the structure using 0 between cycles of refinement. NCS restraints were used between pairs of molecules related by the pseudotranslational symmetry. The working and free R value for the current model for all data to 2.7 Å resolution are 0.23 and 0.28 respectively and the rms deviations from ideal bond lengths and angles are 0.015 Å and 2.1° respectively.

The invention has been disclosed broadly and illustrated in reference to representative embodiments described above. Those skilled in the art will recognize that various modifications can be made to the present invention without departing from the spirit and scope thereof.

We claim:
1. A peptidomimetic having a structure selected from the group consisting of
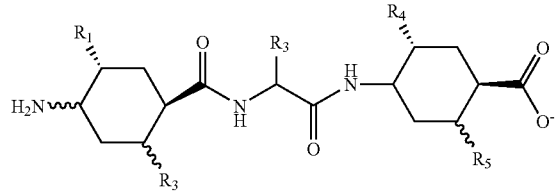
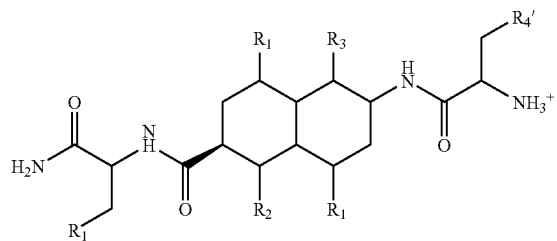
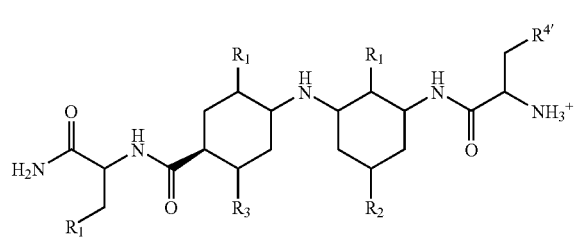
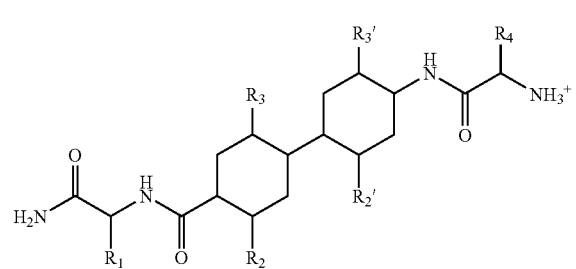
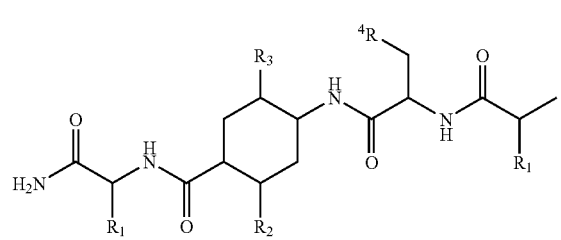
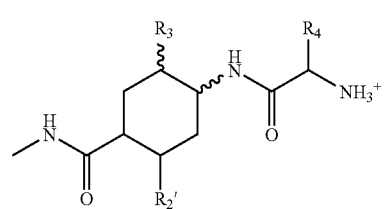
-continued
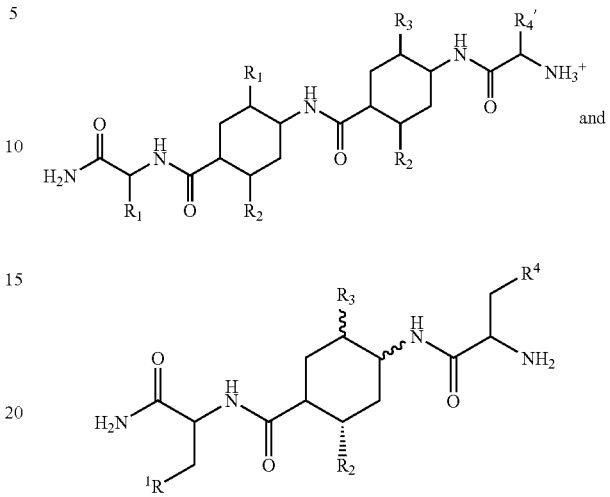
wherein each R group represents H or a portion of a side chain of a natural or unnatural amino acid starting at the gamma carbon.
2. The peptidomimetic of claim 1 having the structure
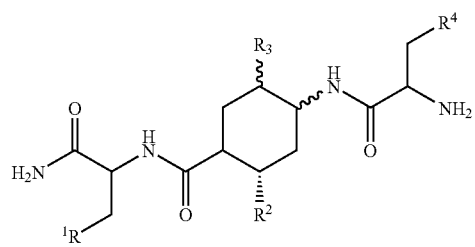
3. A peptidomimetic having a structure selected from the group consisting of
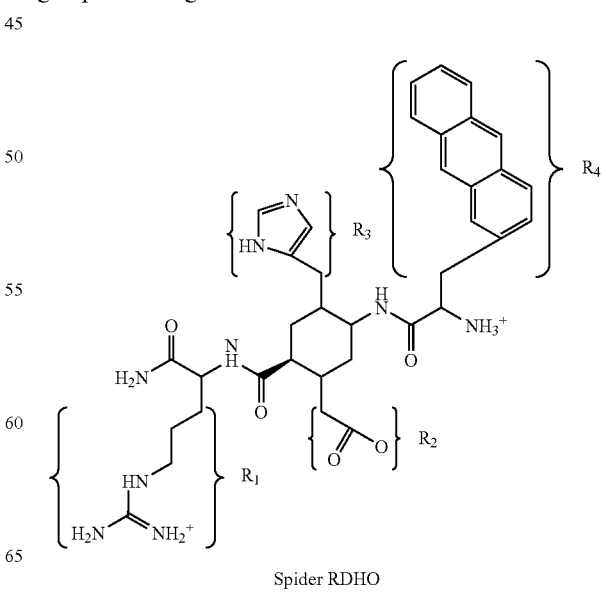
Spider RDHO

-continued
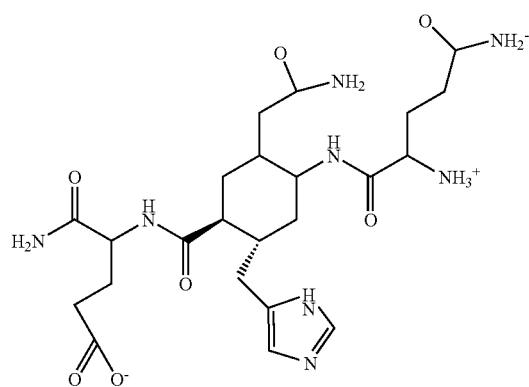
Spider EHNQ (SEQ ID NO: 1)
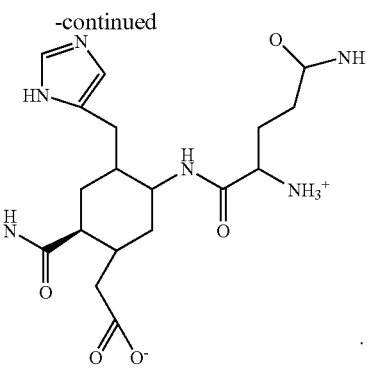
Spider EHNQ (SEQ ID NO: 2)
* * * * *